US005730700A

United States Patent [19]
Walther et al.

[11] Patent Number: 5,730,700
[45] Date of Patent: Mar. 24, 1998

[54] METHOD FOR MEASURING INCIDENT LIGHT IN A BODY CAVITY

[75] Inventors: McClellan M. Walther, Gaithersburg, Md.; Thomas F. DeLaney, Weston, Mass.; Frank Harrington, Catonsville, Md.; Paul D. Smith, Annapolis, Md.; Walter S. Friauf, Bethesda, Md.

[73] Assignee: The United States of America as represented by the Department of Health and Human Service, Washington, D.C.

[21] Appl. No.: 592,440

[22] Filed: Jan. 26, 1996

Related U.S. Application Data

[60] Division of Ser. No. 395,005, Feb. 27, 1995, Pat. No. 5,505,687, which is a continuation-in-part of Ser. No. 294,892, Aug. 22, 1994, Pat. No. 5,575,751, which is a continuation of Ser. No. 883,013, May 14, 1992, abandoned.

[51] Int. Cl.$^6$ ............................................. A61B 1/07
[52] U.S. Cl. .................. 600/104; 600/108; 600/135; 128/653.1; 128/665; 606/11; 606/15
[58] Field of Search ........................ 600/103, 104, 600/108, 118, 135, 105, 182; 128/653.1, 665, 664; 606/11, 12, 15; 356/213, 220, 221, 222

[56] References Cited

U.S. PATENT DOCUMENTS

| | | |
|---|---|---|
| D. 254,270 | 2/1980 | Ziegler . |
| 1,650,959 | 11/1927 | Pitman . |
| 4,066,071 | 1/1978 | Nagel . |
| 4,266,549 | 5/1981 | Kimura . |
| 4,461,283 | 7/1984 | Doi . |
| 4,628,207 | 12/1986 | Elfert et al. . |
| 4,648,892 | 3/1987 | Kittrell et al. . |
| 4,676,231 | 6/1987 | Hisazumi et al. ............... 600/108 |
| 4,681,122 | 7/1987 | Winters et al. . |
| 4,735,501 | 4/1988 | Ginsburgh et al. . |
| 4,756,303 | 7/1988 | Kawashima et al. . |
| 4,784,132 | 11/1988 | Fox et al. . |
| 4,848,323 | 7/1989 | Marijnissen . |
| 4,979,497 | 12/1990 | Matsura et al. . |
| 4,986,622 | 1/1991 | Martinez . |
| 4,988,163 | 1/1991 | Cohen et al. . |
| 4,991,564 | 2/1991 | Takahashi et al. . |
| 5,016,614 | 5/1991 | MacAllister . |
| 5,041,109 | 8/1991 | Abela . |
| 5,050,585 | 9/1991 | Takahashi . |

(List continued on next page.)

FOREIGN PATENT DOCUMENTS 3245845  7/1983  Germany .

OTHER PUBLICATIONS

Nseyo et al, "Whole Bladder Photodynamic Therapy: Critical Review of Present–Day Technology and Rationale for Development of Intravesical Laser Catheter and Monitoring System", Urology, vol. 36: 5, Nov. 1990, pp. 398–402.

Star, Willem M., "Light Delivery and Light Dosimetry for Photodynamic Therapy", Lasers in Medical Science, vol. 5: 107, 1990, pp. 107–112.

Primary Examiner—Richard J. Apley
Assistant Examiner—John P. Leubecker
Attorney, Agent, or Firm—Fish & Richardson P.C.

[57] ABSTRACT

An obturator for measuring incident light in a remote situs such as a body cavity which includes a treatment tubular member through which light is delivered to the remote situs and one or more auxiliary tubular members through which incident light in the remote situs is transmitted to an external light detector. The treatment and auxiliary tubular members are attached to a connector element which is in turn connected to a cystoscope lens port. The treatment and auxiliary tubular members are aligned off-center with respect to the central axis of the obturator so that a cystoscope lens can be inserted in the lens port and pass through the axial center of the obturator. Each auxiliary tubular member receives incident light from a different portion of the remote situs. The apparatus is particularly useful for conducting phototherapy in body cavities and has been demonstrated in the phototherapy treatment of superficial cancer in the bladder.

11 Claims, 3 Drawing Sheets

U.S. PATENT DOCUMENTS

| | | |
|---|---|---|
| 5,099,827 | 3/1992 | Melzer et al. . |
| 5,108,364 | 4/1992 | Takezawa et al. . |
| 5,125,925 | 6/1992 | Lundahl .................................. 606/15 |
| 5,145,863 | 9/1992 | Dougherty et al. . |
| 5,161,531 | 11/1992 | Parsons et al. . |
| 5,188,596 | 2/1993 | Condon et al. . |
| 5,220,927 | 6/1993 | Astrahan et al. . |
| 5,359,685 | 10/1994 | Waynant et al. . |

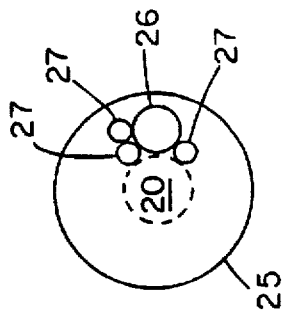
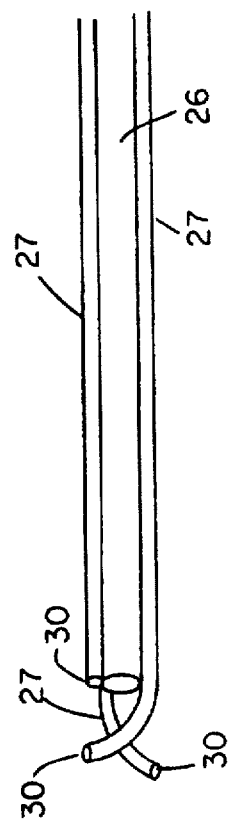
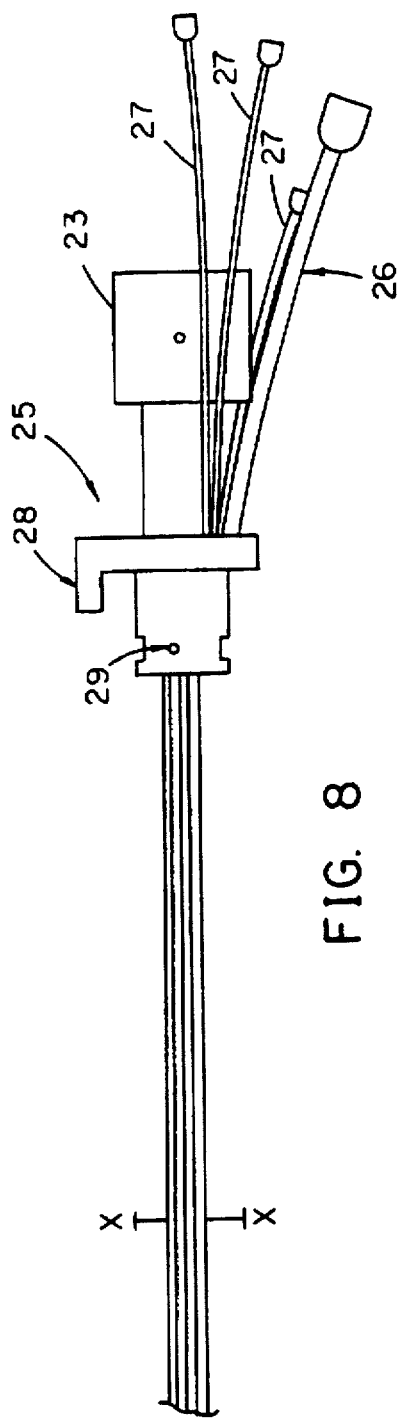

METHOD FOR MEASURING INCIDENT LIGHT IN A BODY CAVITY

RELATED APPLICATIONS

This application is a division of application Ser. No. 08/395,005 filed Feb. 27, 1995, now U.S. Pat. No. 5,505,687, which is a CIP of Ser. No. 08/294,892, filed Aug. 22, 1994, now U.S. Pat. No. 5,575,751, which is a continuation of Ser. No. 07/883,013, filed May 14, 1992, now abandoned.

TECHNICAL FIELD

The present invention relates to phototherapy within a body cavity. More particularly, the present invention relates to methods and apparatus for monitoring light dosage during phototherapy within a body cavity.

BACKGROUND ART

Phototherapy has been found to be an effective method of treating superficial bladder cancer and is expected to find applicability for treatment of similar and other pathological and physiological conditions in other body cavities.

In order to conduct phototherapy within a body cavity a light delivery system is required. Suitable light delivery systems only require a light source such as a laser and an optical fiber to conduct the light to a desired remote position.

To be effective, the light dosage used during ophototherapy must be monitored. Too little light may not provide a desired result. On the other hand, too much light may cause adverse effects, including harm to healthy tissue.

Presently, the only method for monitoring the dosage of light delivered through an optical fiber to a remote location is to monitor the output of light at the light source itself. Such monitoring lacks the accuracy desired in phototherapy.

There exists a need for a method and apparatus which allows for accurate monitoring of light dosage during phototherapy within a body cavity.

SUMMARY OF THE INVENTION

It is accordingly one object of the present invention to provide an apparatus for phototherapy within a remote situs such as a body cavity.

Another object of the present invention is to provide a means for situs viewing and monitoring of light dosage during phototherapy within a remote situs such as a body cavity.

A further object of the present invention is to provide an apparatus for phototherapy within a remote situs such as a body cavity which includes means for viewing the situs and means for situs monitoring of light dosage during phototherapy.

A still further object of the present invention is to provide a method for phototherapy with a remote situs such as a body cavity.

A still further object of the present invention is to provide a method of situs monitoring of light dosage during phototherapy within a remote situs such as a body cavity.

According to these and further objects of the present invention which will become apparent as the description of the present invention is hereafter presented, the present invention provides an obturator which includes:

a cystoscope lens port;

a connector element attached to the cystoscope lens port, the cystoscope lens port and the connector element having a common central axis;

a treatment tubular member having first and second ends; and at least one auxiliary tubular member having first and second ends, wherein each of the at least one auxiliary tubular member is substantially parallel and attached to the treatment tubular member, the first end of each of the at least one auxiliary tubular members is directed in a non-convergent, non-parallel direction with respect to one another, and wherein the treatment and auxiliary tubular members are positioned off-center from the central axis of the cystoscope lens port and the connector element so that a cystoscope lens can be inserted in the lens port and extend thorough the central axis of the cystoscope lens port and the connection element.

The present invention further provides for a method of monitoring incident light in a remote situs which involves:

inserting a treatment tubular member into the remote situs together with at least one auxiliary tubular member which is substantially parallel and attached to an outer surface of the treatment member;

delivering light to the remote situs through the treatment tubular member;

transmitting incident light from the remote situs through the at least one auxiliary tubular member to a light detector; and inserting a cystoscope lens into the remote situs to observe the remote situs while the treatment and the at least one auxiliary tubular members are positioned in the remote situs.

BRIEF DESCRIPTION OF DRAWINGS

The present invention will be described with reference to the attached drawings which are given by way of non-limiting examples only, in which:

FIG. 8 is a schematic view of the end of the obturator of FIG. 7.

FIG. 9 is a schematic view of the tip of the obturator of FIG. 7.

FIG. 10 is a cross-sectional view of the obturator of FIG. 8 taken along line X—X.

BEST MODE FOR CARRYING OUT THE INVENTION

The present invention is directed to an apparatus and method for monitoring light dosage during phototherapy at a remote situs in a body cavity, e.g., in a bladder. The apparatus includes an obturator which is inserted in a cystoscope sheath. The cystoscope sheath utilized in the present invention is of a conventional design. The obturator is of a special design which includes means to deliver light to a remote situs and means to monitor light dosage delivered to the remote situs.

For delivering light to the remote situs, an optical fiber (treatment fiber) is positioned within a central (or "treatment") tubular member in the obturator. The optical fiber extends through the entire length of the obturator and is connected to a suitable light source such as a laser in a conventional manner.

The means to monitor light dosage at the remote situs includes a number of small auxiliary tubular members which are provided adjacent the central tubular member. Each of the auxiliary tubular members is designed with a suitable diameter so that a single, thin optical fiber (dosimetry fiber) can be inserted therein and used to monitor light dosage.

In operation, the obturator tip is positioned in a remote situs such as a body cavity, e.g., a bladder, an optical fiber positioned in the central tubular member delivers light from a light source to the remote situs. Optical fibers within each of the auxiliary tubular members conducts light from the remote situs to a conventional light monitor. In this manner, phototherapy can be conducted while measuring light dosage at the actual, remote situs whereat the phototherapy is occurring.

According to a preferred embodiment of the present invention, the obturator includes a lens port through which a conventional cystoscope lens can be inserted for viewing purposes. In this embodiment, as discussed in detail below, there is no central tubular member. Instead, the "treatment" tubular member and auxiliary tubular members are arranged so that the cystoscope can pass through the lens port and extend adjacent to the treatment and auxiliary tubular members along the axial center of the obturator.

Figure 1:
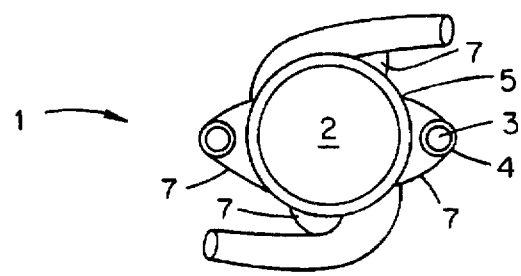
FIG. 1 is a schematic view of the tip of the obturator for a cystoscope according to one embodiment of the present invention.

FIG. 1 is a schematic view of the tip of the obturator for a cystoscope according to one embodiment of the present invention. As depicted in FIG. 1, the obturator 1 includes a central tubular member 2 through which an optical fiber (not shown) can be positioned and utilized to deliver light to a remote situs in the vicinity of the tip of the obturator.

A number of auxiliary tubular members 3 surround and are attached to the central tubular member 2 as shown. The auxiliary tubular members 3 have ends 4 which terminate in the vicinity of the end 5 of the central tubular member 2.

In use, thin, e.g., single strand optical fibers (not shown) are positioned in each of the auxiliary tubular members 3. These optical fibers are utilized to conduct light from the vincity of the tip of the obturator 1 to a conventional light monitor outside of the remote situs.

In the case of monitoring light dosage in a body cavity such as a bladder, it is preferable to monitor light from different quadrants of the cavity. Accordingly, in a preferred embodiment of the invention, each of the ends 4 of the auxiliary tubular members 3 are angled near the end 5 of the central tubular member 2 as shown in FIGS. 1, 2, 5 and 9. This allows the optical fibers positioned in the auxiliary tubular members 3 to receive light from different areas in the body cavity. It is noted that the tips of the optical fibers positioned in the auxiliary tubular members 3 can extend beyond the ends 4 of the auxiliary tubular members 3 or otherwise be substantially flush with the ends 4 of the auxiliary tubular members 3.

Figure 2:
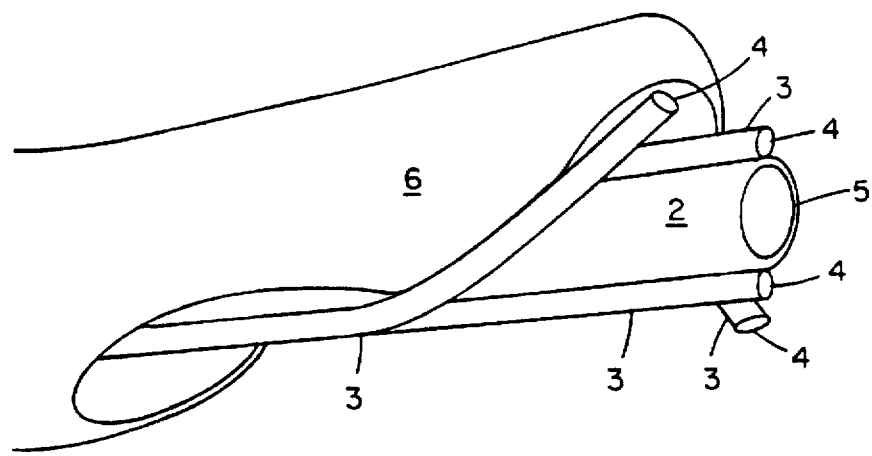
FIG. 2 is a perspective view of the tip of an obturator of the present invention which is positioned in a sheath of a cystoscope.

FIG. 2 is a perspective view of the tip of the obturator positioned in a sheath of a cystoscope. The cystoscope sheath 6 shown in FIG. 2 is of a conventional design and is merely utilized to position the obturator 1 in a remote situs whereat phototherapy is to be conducted.

FIG. 2 (and FIG. 5) show how the auxiliary tubular members 3 are positioned adjacent the central tubular member 2 and how the ends 4 of the auxiliary tubular members 3 are directed at different angles from each other.

In fabricating the obturator utilizing a rigid material such a metal, e.g., surgical steel, a number of auxiliary tubular members 3 are positioned parallel above the central tubular member 2 and affixed thereto by soldering, cementing, e.g., epoxying, or other equivalent means. At the tip of the obturator, the ends of the auxiliary tubular members 3 are bent at the end of the central tubular member so as to project at different angles from each other, as discussed above.

In FIG. 1, a weld portion 7 is provided for illustrative purposes. The welded portion is not shown in FIG. 2 so that the relative arrangement of the central tubular member 2 and the auxiliary tubular members 3 is visible.

It is preferable to utilize a sterilizable material such as a metal from which to fabricate the obturator 1 so that the obturator 1 can be sterilized and reused. However, it is also possible to fabricate the obturator 1 from other biocompatible materials including plastics and resinous materials. The main concern in utilizing such materials is ensuring that they are not adversely effected by heat from the light utilized in the phototherapy. It is also possible to form the auxiliary tubular members 3 so that they are integral with the wall of the central tubular member 2.

For illustrative purposes, the drawings show the use of four auxiliary tubular members 3. However, it is to be noted that any number of auxiliary tubular members 3, including a single auxiliary tubular member, could be utilized.

Figure 3:
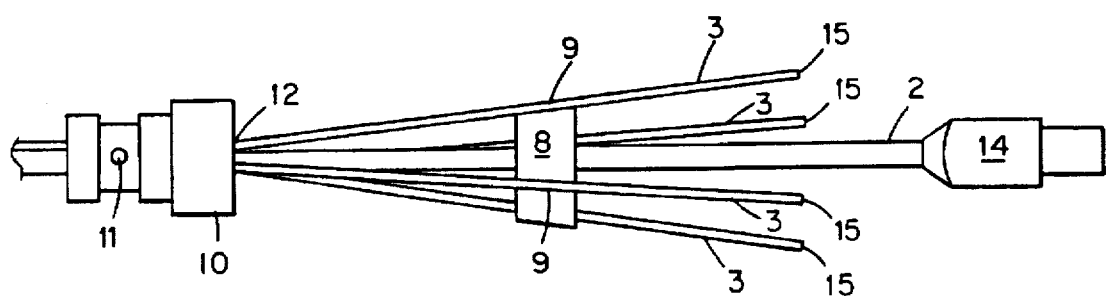
FIG. 3 is a schematic view of the end of the obturator for a cystoscope according to one embodiment of the present invention.
Figure 5:
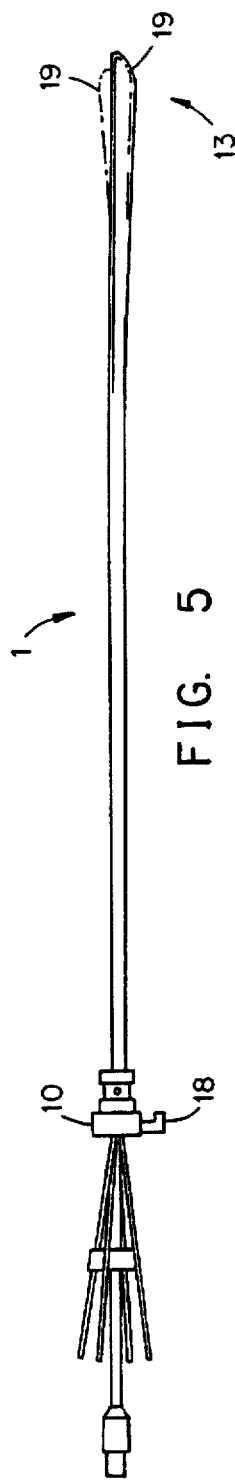
FIG. 5 is a schematic view of the obturator of FIG. 3.

FIG. 3 is a schematic view of the end of the obturator 1 for a cystoscope according to one embodiment of the present invention. At the end of the obturator 1 the ends 15 of the auxiliary tubular members 3 are ideally separated from one another. FIG. 3 shows the use of a spacer 8 in the form of a frustrum of a cone which is used to maintain separation of the ends of the auxiliary tubular members 3. The spacer 8 has a number of grooves 9 therein into which the auxiliary tubular members 3 are seated, as shown. The obturator 1 includes a connector 10 by which the obturator 1 is connected to the cystoscope sheath 6 as discussed below. This connector 10 is of a conventional design and includes locking pins 11 which are use to secure the obturator 1 to the cystoscope sheath 6. From the end 12 of the connector 10 to the tip 13 of the obturator 1 the auxiliary tubular members 3 are closely adjacent the central tubular member 2 as shown in FIG. 5.

The central tubular member 2 includes a conventional coupler 14 by which an optical fiber (treatment fiber) can be inserted into to the central tubular member 2 and secured therein. Optical fibers (dosimeter fibers) are inserted though the ends 15 of the auxiliary tubular members 3. It is for this reason that the ends 15 of the auxiliary tubular members 3 are separated from one another. Such separation allows access to the ends 15 of each of the auxiliary tubular members 3.

Although not illustrated the free end of an optical fiber positioned within the central tubular member 2 is connected to a conventional light source such as a laser. Likewise the free ends of the optical fibers inserted in the auxiliary tubular members 3 are connected to one or more conventional light monitors. In a preferred embodiment, light is simultaneously monitored from each of the optical fibers inserted in the auxiliary tubular members 3. In other embodiments, light from one or more of the optical fibers inserted in the auxiliary tubular members 3 is monitored. It is also possible to alternatively scan each of the optical fibers inserted in the auxiliary tubular members 3 periodically or selectively.

Figure 4:
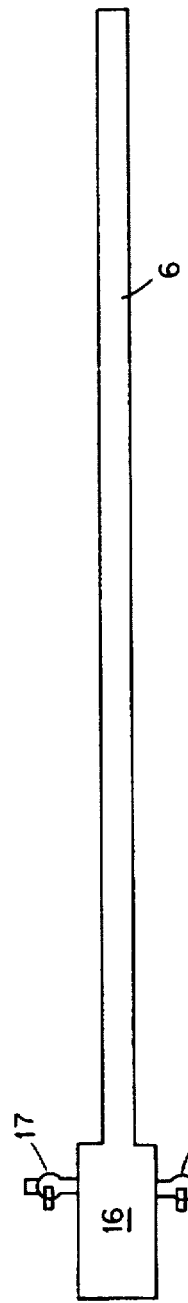
FIG. 4 is a schematic view of a cystoscope sheath.

FIG. 4 is a schematic view of a cystoscope sheath. The cystoscope sheath 6 is of conventional design and includes a connector element 16 in which the obturator 1 is inserted and to which the obturator 1 is attached. Conventional valved ports 17 are provided on the connector 16.

FIG. 5 is a schematic view of the obturator according to one embodiment of the present invention. In FIG. 5 the connector element 10 is shown as including a lever 18 by which the obturator 1 is connected to the connector 16 of the cystoscope sheath 6. In this regard, in a conventional manner, once connector element 10 is inserted into connector element 16, relative rotation of the connecting elements causes locking pins 11 (FIG. 3) to engage locking recesses or cams in connecting member 16. In alternative embodiments, other conventional connecting means could also be used.

In FIG. 5 the curved ends 19 of the auxiliary tubular members 3 are slightly exaggerated so as to show how they are directed to point in different directions.

Figure 6:
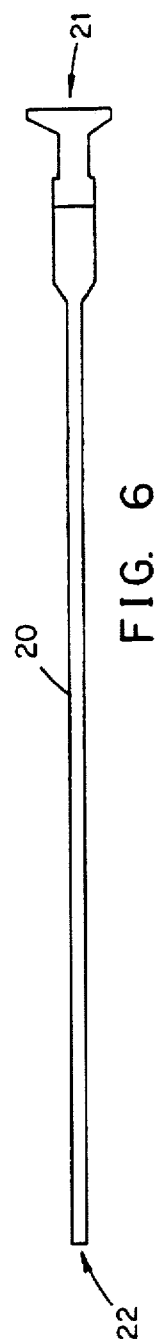
FIG. 6 is a schematic view of a cystoscope lens.

FIG. 6 is a schematic view of a cystoscope lens. The cystoscope lens 20 is of conventional design and includes a viewing aperture 21 on an end thereof through which an operator can observe a visual field at the opposite end 22 of the lens. In use, the cystoscope lens 20 is received and secured in the lens port 23 of the obturator of FIG. 7. In this regard, the lens port 23 of the obturator is of conventional design.

Figure 7:
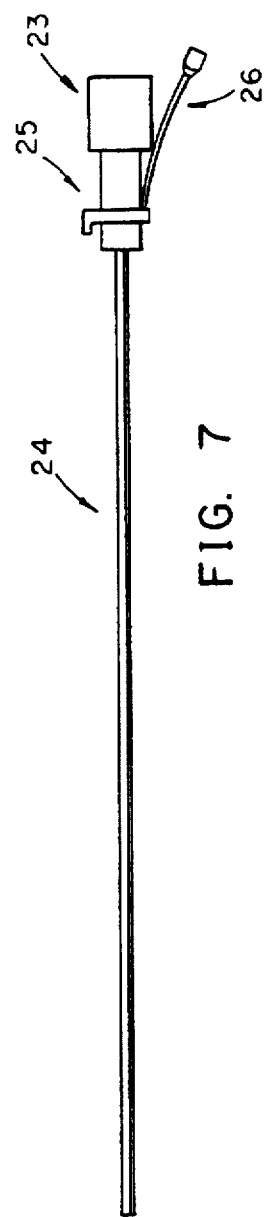
FIG. 7 is a schematic view of an obturator according to a further embodiment of the present invention.

FIG. 7 is a schematic view of an obturator according to a further embodiment of the present invention. This obturator 24 includes a lens port 23 which receives the cystoscope lens 20 in a conventional manner, as discussed above. The lens port 23 is connected to an conventional connector element 25 by which the obturator 24 can be connected to the cystoscope sheath of FIG. 4. In this embodiment, the connector element 25 has been modified so than a treatment tubular member and a plurality of auxiliary tubular members pass through a rear portion of the connector element 25. For illustrative purposes, one tubular member is shown passing through a rear portion of the connector element 25 in FIG. 7.

FIG. 8 is a schematic view of the end of the obturator 24 of FIG. 7 which shows more details of the obturator 24. As can be seen in FIG. 8, the treatment tubular member 26 and the auxiliary tubular members 27 enter the obturator through a rear side portion in between the lens port 23 and the connector element 24. For example, separate, angled bores are made in the rear portion of the connector element 23 through which the treatment tubular member 26 and the auxiliary tubular members 27 are inserted. Preferably these bores do not intersect the main bore through the connector element 25. Alternatively, the bores for the tubular members could intersect the central bore of the connector element 25, as long as a sealing connection for the cystoscope lens is provided by the lens port 23. In FIG. 8 the treatment tubular member is shown passing through the connector element 25 in broken lines.

The treatment tubular member 26 and the auxiliary tubular members 27 pass through the connector element 25 in such a manner so that they do not obstruct the axial center of the connector member 25. This is important, because the cystoscope lens 20 should pass through the axial center of the connector element 25 (and lens port 23) when it is received in the obturator 24. The particular arrangement of the treatment tubular member 26 and the auxiliary tubular members 27 is discussed below with reference to FIGS. 9 and 10.

The obturator of FIG. 7 includes a lever 28 and locking pins 29 by which it can be connected to the connector element 16 of the cystoscope sheath 6. In this regard, in a conventional manner, once connector element 25 is inserted into connector element 16, relative rotation of the connecting elements causes locking pins 29 to engage locking recesses or cams in connecting member 16. In alternative embodiments, other conventional connecting means could also be used.

FIG. 9 is a schematic view of the tip of the obturator of FIG. 7. FIG. 9 shows how the auxiliary tubular members 27 are positioned adjacent the treatment tubular member 26 and how the ends 30 of the auxiliary tubular members 27 are directed at different angles from each other.

In fabricating the obturator utilizing a rigid material such as metal, e.g., surgical steel, a number of auxiliary tubular members 27 are positioned parallel to the treatment tubular member 26 and affixed thereto by welding, cementing, e.g., epoxying, or other equivalent means. At the tip of the obturator, the ends of the auxiliary tubular members 27 are bent at the end of the treatment tubular member 26 so as to project at different angles from each other, as discussed above.

FIG. 10 is a cross-sectional view of the obturator of FIG. 8 taken along line X—X. In FIG. 10 the position of the cystoscope lens 20 is shown in broken lines. FIG. 10 shows how the treatment tubular member 26 and auxiliary tubular members 27 are arranged and connected to one another so as to allow the cystoscope lens 20 to pass through the central axis of the obturator. In FIG. 10, the connector element 25 of the obturator is provided to illustrate the axial position of the cystoscope lens 20.

It is to be understood that the obturator 24 of FIGS. 7-10 can include any number of auxiliary tubular members 27, even a single auxiliary tubular member.

The device of the present invention has been tested in a procedure in which superficial bladder cancer was subject to phototherapy. In use, the obturator is placed in the cystoscope sheath and positioned in the bladder. The treatment fiber is inserted in the central tubular member and dosimeter fibers are inserted into each of the auxiliary tubular members. Light was supplied to the free end of the treatment fiber which delivered the phototherapy light to the wall(s) of the bladder. Light dosage within the bladder was monitored by transmitting light received by the dosimeter fibers to a light monitor.

In tests, it was determined that the use of the obturator of the present invention to monitor light dosage within a bladder was more accurate and reliable that monitoring the intensity of the light source outside of the subject's body.

The obturator of the present invention and the manner in which it was tested are applicable for use in any remote cavity in which a measurement of light intensity is desired. The device and its method of use are not limited to cavities in a subject's body.

Although the present invention has been described with reference to particular means, materials and embodiments, from the foregoing description, one skilled in the art can easily ascertain the essential characteristics of the present invention and various changes and modifications may be made to adapt the various uses and characteristics without departing from the spirit and scope of the present invention as described by the claims which follow.

What is claimed is:

1. A method of monitoring incident light in a remote situs which comprises:

inserting a treatment tubular member into said remote situs together with at least one auxiliary tubular member, each having first and second ends, and being substantially parallel and attached to an outer surface of said treatment member, wherein each first end is directed in a non-convergent, nonparallel direction with respect to any other auxiliary tubular member and with respect to said treatment tubular member;

delivering light to said remote situs through said treatment tubular member;

transmitting incident light from said remote situs through said at least one auxiliary tubular member to a light detector wherein the first end of each auxiliary tubular member is not in direct physical contact with tissue at said remote situs; and inserting a cystoscope lens into said remote situs to observe said remote situs while said treatment and said at least one auxiliary tubular members are positioned in said remote situs.

2. A method of monitoring incident light in a remote situs according to claim 1, wherein said at least one auxiliary tubular member comprises more than one auxiliary tubular member.

3. A method of monitoring incident light in a remote situs according to claim 2, wherein each of said at least one auxiliary tubular members receives incident light from a different portion of said remote situs.

4. A method of monitoring incident light in a remote situs according to claim 2, wherein said remote situs comprises a body cavity.

5. A method of monitoring incident light in a remote situs according to claim 4, wherein said body cavity comprises a bladder.

6. A method of monitoring incident light in a remote situs according to claim 2, wherein light is conducted through each of said treatment and at least one auxiliary tubular members by means of optical fibers.

7. A method of monitoring incident light in a remote situs according to claim 2, wherein said at least one auxiliary tubular member comprises three auxiliary tubular members.

8. A method of monitoring incident light in a remote situs according to claim 2, wherein said incident light measurement is utilized to monitor a phototherapy procedure.

9. A method of monitoring incident light in a remote situs according to claim 2, wherein a hollow sheath is used to insert said treatment and at least one auxiliary tubular members into said remote situs.

10. A method of monitoring incident light in a remote situs according to claim 2 wherein insertion of said cystoscope lens into said remote situs includes inserting said cystoscope lens into a lens port which is connected to said treatment and at least one auxiliary tubular members.

11. A method of monitoring incident light in a remote situs comprising:

inserting a treatment tubular member into a remote situs together with at least one auxiliary tubular member each of which is substantially parallel and attached to an outer surface of said treatment member and which has a first end that is directed in a non-convergent, nonparallel direction with respect to any other auxiliary tubular member and with respect to said treatment tubular member;

delivering light to said remote situs through said treatment tubular member;

transmitting incident light from said remote situs through at least one such auxiliary tubular member to a light detector wherein the first end of each auxiliary tubular member is not in physical contact with tissue at said remote situs; and inserting a cystoscope lens into said remote situs to observe said remote situs while said treatment and said auxiliary tubular members are positioned in said remote situs; and wherein each auxiliary tubular member receives incident light from a different portion of said remote situs; and wherein insertion of said cystoscope lens into said remote situs includes inserting said cystoscope lens into a lens port, which is connected to said treatment and at least one auxiliary tubular member.

* * * * *